United States Patent [19]

Gioffre et al.

[11] Patent Number: 4,818,518

[45] Date of Patent: * Apr. 4, 1989

[54] EFFERVESCENT DENTIFRICE

[75] Inventors: Anthony J. Gioffre, Ridgefield, Conn.; Ronald J. Ross, Upper Nyack, N.Y.

[73] Assignee: UOP, Des Plains, Ill.

[*] Notice: The portion of the term of this patent subsequent to Dec. 9, 2003 has been disclaimed.

[21] Appl. No.: 928,014

[22] Filed: Nov. 7, 1986

Related U.S. Application Data

[62] Division of Ser. No. 672,351, Nov. 16, 1984, Pat. No. 4,627,972.

[51] Int. Cl.$^4$ .................................................. A61K 7/16
[52] U.S. Cl. ........................................ 424/44; 424/43; 424/59; 424/52
[58] Field of Search ......................... 424/43, 44, 49-58

[56] References Cited

U.S. PATENT DOCUMENTS

| | | | |
|---|---|---|---|
| 3,250,680 | 5/1966 | Menkart et al. | 167/85 |
| 3,574,824 | 4/1971 | Echeandia | 424/50 |
| 4,066,745 | 1/1978 | Tomlinson et al. | 424/49 |
| 4,132,771 | 1/1979 | Schreiber | 424/52 |
| 4,153,680 | 5/1979 | Seybert | 424/49 |
| 4,159,316 | 6/1979 | Altan et al. | 424/49 |
| 4,187,287 | 2/1980 | Schreiber et al. | 424/49 |
| 4,193,987 | 3/1980 | Harth et al. | 424/49 |
| 4,209,504 | 6/1980 | Harth et al. | 424/49 |
| 4,349,533 | 9/1982 | Dent et al. | 424/50 |
| 4,537,764 | 8/1985 | Pellico et al. | 424/50 |
| 4,574,052 | 3/1986 | Gupte et al. | 252/90 |
| 4,627,972 | 12/1986 | Gioffre et al. | 424/49 |

FOREIGN PATENT DOCUMENTS

| | | |
|---|---|---|
| 333142 | 8/1930 | United Kingdom . |
| 1304090 | 1/1973 | United Kingdom . |
| 1382898 | 2/1975 | United Kingdom . |
| 2082454A | 3/1982 | United Kingdom . |
| 2109682A | 6/1983 | United Kingdom . |

Primary Examiner—Johnnie R. Brown
Assistant Examiner—F. T. Moezie
Attorney, Agent, or Firm—Richard G. Miller

[57] ABSTRACT

Dentifrice compositions are provided having an effervescent and cleansing action. The dentifrice compositions are formed from an essentially anhydrous dentifrice base medium and an inorganic oxide material containing an adsorbed gas. Upon contact of the dentifrice composition with water, an effervescent action occurs as the gas is desorbed from the inorganic oxide material.

10 Claims, No Drawings

EFFERVESCENT DENTIFRICE

This application is a division of Ser. No. 672,351, filed Nov. 16, 1984, now U.S. Pat. No. 4,627,972.

The invention relates to the field of dentifrice compositions and to the process for the cleansing of teeth and the oral cavity by use an essentially anhydrous dentifrice containing at least one gas-containing inorganic oxide material.

The development and formulation of dentifrice compositions has resulted in many dentifrice compositions directed to improving some particular physical and/or chemical characteristic of such dentifrice compositions. One area of interest has been in the area of anti-plaque and anti-calculus dentifrices. Such dentifrice compositions are disclosed in the literature, including patents.

One early attempt to provide a zeolite-containing dentifrice is disclosed in U.K. Pat. No. 332,142, dated July 17, 1930. The dentifrice contained a zeolite and a carbonate salt. The zeolite was provided as a means of removing calcium and/or magnesium cations which may form insoluble carbonates.

Another area of interest has been dentifrice compositions capable of generating a warming sensation when introduced into the oral cavity. Such a warming can be provided by the chemical reaction of two reagents in an exothermic reaction or may be provided by the hydration of an anhydrous zeolite. U.S. Pat. No. 3,250,680 discloses anhydrous heat-generating cosmetic compositions containing an anhydrous solid particulate absorbent material. The absorbent material is capable of sorbing water exothermically and may be silica gel, activated alumina and/or alkali metal aluminosilicate molecular sieves. U.S. Pat. No. 4,159,316 discloses a "self-heating dentifrice". The dentifrice composition is anhydrous and contains as the sole or major polishing agent a finely divided anhydrous synthetic zeolite having an appreciable heat of hydration. The dentifrice provides the heat of hydration of the zeolite for warming the dentifrice when such is introduced to a water-containing environment. U.S. Pat. Nos. 4,132,771 and 4,187,287 disclose anhydrous dentifrice compositions similar to the dentifrice compositions of U.S. Pat. No. 4,159,316.

Although considerable effort has been made to improve the various cleaning and aesthetic characteristics of dentifrice compositions, one area for improving both the cleansing action and aesthetic nature of dentifrice compositions has found little development. This area relates to the development of effervescent dentifrice compositions. U.S. Re. Pat. No. 14,961, reissued Oct. 19, 1920 on U.S. Pat. No. 1,297,494, disclosed a dentifrice containing a solid acidic substance and a carbonate. The chemical action of the compounds provide an effervescence. U.S. Patent No. 3,629,468 discloses an effervescent mouthwash tablet. The mouthwash tablet contains an acid compound and a salt capable of evolving carbon dioxide when brought into aqueous reactive contact with the acid component.

The instant invention comprises dentifrice compositions that provide effervescent cleansing and enhanced aesthetic enjoyment by the user.

SUMMARY OF THE INVENTION

Dentifrice compositions are disclosed that provide an effervescent/mechanical-cleaning action during use. The dentifrice compositions comprise an essentially anhydrous dentifrice base medium and an inorganic oxide material containing an effective amount, generally up to about 25 percent by weight, of an adsorbed gas, e.g., carbon dioxide. The dentifrice compositions also provide an astringent sensation in the oral cavity as a result of the effervescent cleaning action and when carbon dioxide is the adsorbed gas by the in situ generation of carbonic acid.

DETAILED DESCRIPTION OF THE INVENTION

The invention relates to essentially anhydrous dentifrice compositions which provide an effervescent action and mechanical cleansing action when introduced to the oral cavity in the presence of water. This effervescent action is both stimulating to the oral cavity and provides a mechanical action which enhances cleaning and effective distribution of the active dentifrice components throughout the oral cavity. The dentifrice compositions are formed from an essentially anhydrous dentifrice base medium and a gas-containing inorganic oxide material, preferably a gas-containing aluminosilicate.

The dentifrice compositions of the instant invention are unique in providing effervescent action without the need of chemical acid/base reactions as heretofore employed in dentifrice compositions. The dentifrice compositions are formed by use of an inorganic oxide material, e.g., microporous molecular sieves, having an effective amount of adsorbed gas such that when contained in an essentially anhydrous dentifrice that is contacted with water a release of the adsorbed gas occurs to provide an effervescent effect as the adsorbed gas is desorbed. The inorganic oxide material, preferably a microporous inorganic oxide material, employed in the dentifrice compositions are usually at least partially dehydrated, i.e., such inorganic oxide materials have had at least a portion of their chemically reactive water removed by thermal or chemical treatment. Such materials may be prepared by calcination of the hydrated materials at temperatures above 100° C. in air or other gas. Dehydration of the inorganic oxide material may be carried out at temperatures below 100° C. when subatmospheric pressures are employed. The preparation of carbon dioxide-containing zeolites is disclosed in British Pat. No. 1,382,896, incorporated herein by reference thereto, at pages 2 to 5, inclusive, and such preparation may be employed in the instant invention. The dehydrated inorganic oxide materials preferably contain less than about 10 percent by weight water, and more preferably less than about 5 percent by weight. The use of such dehydrated materials also may provide dentifrice compositions which provide a warming sensation on use, since many such materials, e.g., dehydrated zeolites, exothermically react with water. Such exothermic reactions may be beneficial in increasing the rate of desorption of adsorbed gas.

The dentifrice compositions of the instant invention comprise an essentially anhydrous dentifrice base medium and a gas-containing inorganic oxide material. The gas may be any gas capable of being adsorbed by the inorganic oxide material in sufficient effective amount to provide effervescent action upon contacting of the dentifrice composition with water. The adsorbed gas is generally present in an amount between about 1 and 25 weight percent of the total weight of the adsorbed gas and inorganic oxide material. Since the effervescent action of the desorbing gas provides a mechanical cleaning and mixing action in the oral cavity it is preferred to have between about 5 and 25 weight percent of the adsorbed gas present, based on the total weight of inorganic oxide material and adsorbed gas. Upon contacting the essentially anhydrous dentifrice composition with water, e.g., saliva, the adsorbed gas will be released and an effervescent action occurs.

The inorganic oxide material may be any material capable of adsorbing an effective amount of a gas which upon contact with water desorbs the gas in favor of the adsorption of water. The inorganic oxide material can be any of the zeolitic aluminosilicates capable of adsorbing an effective amount of a gas, an aluminophosphate, e.g., as disclosed in U.S. Pat. No. 4,310,440, a silicoaluminophosphate, e.g., as disclosed in U.S. Pat. No. 4,440,871, aluminas, silicas, silicates, silicalite, silica aluminas and the like. The inorganic oxide material is preferably a microporous material since microporous materials demonstrate gas adsorption characteristics as a result of the pore structure of the material. Representative of such materials are zeolite A, zeolite B, zeolite X, zeolite Y, zeolite P, zeolite W, zeolite L, zeolite F, ZSM-type zeolites, silicalite, natural zeolites such as analcite, chabazite, clinoptilolite, errionite, paulingite, ptilolite, ferrierite, mordenite, levynite, etc., and mixtures thereof. The zeolite may contain cations of alkali metals, alkaline earth metals, zinc, copper, etc., or any other cation suitable for dentifrice compositions. The gas-containing inorganic oxide material may be present in the dentifrice composition in an effective amount between about 1 percent and about 99 percent by weight (wt. %) of the total weight of the dentifrice composition and is typically present in an amount between about 1 wt. % and about 60 wt. % and preferably between about 5 wt. % and about 50 wt % of the dentifrice composition. The gas-containing inorganic oxide material may also act as an abrasive and preferably has an RDA (Radioactive Dentin Abrasion) value less than 250, more preferably between about 30 and about 150 and most preferably between about 30 and about 120. The mechanical cleaning action of the desorbing gas may allow for the use of abrasives, including the gas-containing inorganic oxide material, having lower RDA values. The mean particle size of the gas-containing inorganic oxide material is preferably less than 10 microns and preferably has a particle size distribution with less than 10 percent, more preferably less than 5 percent by weight of the particles having a particle diameter greater than 5 microns.

The gas to be employed on this instant invention may be any gas which is a gas at 18° C. and above and which when adsorbed by the inorganic oxide material will then desorb upon being contacted with water. The gas may be, but is not limited to, nitrogen, oxygen, helium, argon, carbon dioxide, and the like and mixtures thereof. The preferred gas is carbon dioxide owing to its ability to form carbonic acid when it contacts water and thus provide an astringent effect.

The preferred gas-containing inorganic oxide material is a carbon dioxide-containing aluminosilicate formed by contacting an at least partially dehydrated aluminosilicate with carbon dioxide under effective conditions that result in the adsorption of carbon dioxide by the aluminosilicate. The aluminosilicate, preferably anhydrous, will typically have absorbed between about 1 and about 25 percent by weight carbon dioxide, based on the total weight of said carbon dioxide and aluminosilicate. The aluminosilicate preferably adsorbs between about 5 and about 20 percent by weight carbon dioxide. The most preferred aluminosilicates are the zeolites: zeolite A; zeolite X; and zeolite Y. In addition to the effervescent action of the gas-containing zeolite, anhydrous zeolites are observed to exothermically react with water upon contact with water and provide the dentifrice composition with a warming action. This warming action also enhances the rate of desorption of the gas from the zeolite.

The dentifrice compositions are formed with an essentially anhydrous dentifrice base medium as heretofore employed in the formulations of anhydrous dentifrice compositions. Representative formulations are disclosed in U.S. Pat. No. 3,250,680. The term "essentially anhydrous" is meant to denote a dentifrice base composition, either liquid or solid, that has a water content sufficiently low so as not to cause the adsorbed gas to be desorbed from the inorganic oxide material prior to contac with water. The essentially anhydrous dentifrice base medium can include flavor components, coloring agents, polishing agents, fluorine-containing compounds, humectants, thickeners, abrasives, organic surface-active agents and the like.

Any suitable flavoring or sweetening agent or mixture thereof may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon, lime, grapefruit and orange as well as flavoring aldehydes, esters such as methyl salicylate, alcohols, and higher fatty compounds known in the art. Also useful are such chemicals as menthol, carvone and anethole. Of these, the most commonly employed are the oils of peppermint, spearmint, and eucalyptus, and anethole, menthol and carvone. In some cases flavorful solvents, such as chloroform and mock chloroform, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liguid form, if so desired, by dissolving it in a solvent or emulsifying it, usually with the help of asynthetic or natural emulsifying agent. The choice as to whether to utilize particulate solid or liquid flavors or to convert such flavors to a particulate solid or liquid form, respectively, will often depend on the properties desired in the flavor and its compatibility with the sweetener and any other material to be present with it. Suitable sweetening agents include mannitol, sucrose, lactose, maltose, sorbitol, xylitol, sodium cyclamate, saccharin, the dipeptides of the U.S. Pat. No. 3,939,261 and the oxathiazin salts of U.S. Pat. No. 3,932,606. Suitably, flavor and sweetening agent may together comprise from about 0.1 to 10% or more of the compositions of the instant invention.

The dentifrice compositions of this invention may also include an additional dentally acceptable, substantially water insoluble anhydrous polishing agent of the type commonly employed in dental creams as a part of the abrasive system. Such polishing agents are usually finely divided water insoluble powdered materials. Such are generally from 1 to 40 microns and typically from about 2 to about 20 microns in particle size with the distribution of normal particle sizes being over the range. Representative polishing agents include, for example, dicalcium phosphate, tricalcium phosphate, insoluble sodium metaphosphate, aluminum hydroxide, colloidal silica, SYLOID 74 (a micron sized synthetic silica) magnesium carbonate, calcium carbonate, calcium pyrophosphate, bentonite, amorphous aluminosilicate, etc., including suitable mixtures thereof. Such additional polishing agents may be present in an amount up to a maximum of 95% by weight of the formulation, e.g., when a powdered formulation is desired, and are preferably present in an amount no more than 50%, the amount depending on the desired abrasivity and characteristics of the dentifrice composition.

The dentifrice compositions of the present invention may optionally contain a fluorine-containing compound having a beneficial effect on the care and hygiene of the oral cavity, e.g., diminution of enamel solubility in acid and protection of the teeth against decay. Examples thereof include sodium fluoride, stannous and manganese fluoride, potassium fluoride, potassium stannous fluoride ($SnF_2KF$), sodium hexafluorostannate, stannous chlorofluoride, sodium or potassium fluorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof. Sodium fluoride and sodium monofluorophosphate are particularly preferred as well as mixtures thereof. The effervescent and mechanical action of the instant dentifrice compositions in the mouth may enhance the effectiveness of fluoride and thereby enhance the anti-cavity and anti-stain properties of the dentifrice compositions.

The dentifrice compositions of this invention include liquids and solids that may be proportioned to form a creamy mass of desired consistency which is extrudable from an aerosol or other pressurized container or a collapsible tube (for example aluminum). In general, the liquid vehicle in dental cream formulations will comprise glycerine, oils, propylene glycol, polyethylene glycol 400, etc. and the like, including suitable mixtures thereof. The total liquid content will generally be about 20 to 75 percent by weight of the dentifrice composition. A gelling agent in dental creams and gels may be employed, such as the natural and synthetic gums and gum-like materials, for example, Irish moss, gum tragacanth, methyl cellulose, polyvinylpyrrolidone, hydrophilic colloidal carboxyvinyl polymers such as those sold under the trademark Carbopol 934 and 940, hydroxyethyl cellulose, Indian gum, acacia gums, agar, locust bean gum, synthetic silicated clays such as those sold under the trademark Laponite CP and Laponite SP, pectin and finely divided pyrogenic silica, sold under the trademarks CAB-O-SIL M5, SYLOID 244, SYLOID 266 and AEROSOL D 200.

The proportions of gelling agents or thickeners in extrudable dentifrices are sufficient to form an extrudable, shape-retaining product which can be squeezed from a tube onto a toothbrush and will not fall between the bristles of the brush but rather, will substantially maintain its shape thereon. In most cases no more than about 10% of gelling agent need be used and in most instances about 0.5 to 10% will suffice, and preferably about 1 to 5%.

Suitable oils for use in form dentifrice compositions include those which have viscosities ranging from about 100 to about 300 centipoises at 70° F. Oils employable herein include mineral oil, light liquid petrolatum thickened to the necessary viscosity; and vegetable oils. A mineral oil commonly employed in dentifrice compositions is Mineral Oil U.S.P. also known as Liquid Petrolatum U.S.P., mineral oil (heavy medicinal) white mineral oil, liquid paraffin, and heavy liquid petrolatum. Mineral oil U.S.P. is defined in Remington's Pharmaceutical Sciences, 13th edition, Mack Publishing Co., Easton, Pa. 1965 as "a mixture of liquid hydrocarbons obtained from petroleum; a colorless transparent, oily liquid, free or nearly free from fluoroescene". It is tasteless and odorless when cold and develops not more than a faint odor of petroleum when heated.

A light liquid petrolatum employable herein is Light Liquid Petrolatum N.F. also known as light liquid paraffin and light white mineral oil. It is described in Remington's Pharmaceutical Sciences, as ". . . a mixture of liquid hydrocarbons obtained from petroleum, it may contain a stabilizer". If Light Liquid Petrolatum N.F. is used as the oil it may be thickened to the desired viscosity of from about 100 to about 300 centipoises at 70° F with one of the well-known commercially available inert thickening materials, such as a pyrogenic silica sold under the trademark CAB-O-SIL, or a hydrogenated castor oil, sold under the tradename THIXIN.

Suitable vegetable oils which may be used as the oil ingredient include coconut oil, cotton-seed oil, sesame oil and similar non-toxic vegetable oils, as described in Vegetable Fats and Oils by E. W. Eckey, Reinhold Publishing Corp., New York, 1954. The vegetable oil is desirably selected to fall within the viscosity range of from about 100 to about 300 centipoises. A particular vegetable oil falling within this range is NEOBFE M -5, a fractional triglyceride of coconut oil. The vegetable oil ingredient may contain a minor amount of an anti-oxidant such as butylated hydroxyanisole or butylated hydroxytoluene, preferably in an amount ranging from about 0.1% to about 3% by weight, based on the weight of the vegetable oil employed.

The liquid vehicle of an extrudable dentifrice, together with the gelling agent(s) and other constituents, will form an extrudable mass of a non-dripping consistency when extruded from a collapsible tube, such as an aluminum tube. Thus, by the addition of more vehicle, the dental cream can be thinned and conversely, by the addition of more solids, especially more gelling agents and/or gas-containing inorganic oxide material, the dentifrice compositions can be thickened. It is preferred to employ glycerine in the instant dentifrice compositions, although other suitable vehicles in place thereof or in addition thereto may also be present. Thus, propylene glycol, polyethylene glycol, and polypropylene glycol may be employed providing that they are physiologically acceptable and produce products having a desired refractive index, in the case of the manufacture of visually clear dentifrices. The use of glycerine in the liquid vehicle is particularly advantageous in acting with the aluminosilicate component in effecting utilization of the flavor components of the dentifrice composition. Normally the proportion of vehicle is determined by the physical properties of the extrudate. Usually, however, from about 10 to 90% of the vehicle will be employed, with about 10 to 35% being a typical range for the production of opaque dentifrices and about 40 to 90% being useful for the manufacture of clear dental preparations.

It is to be understood that while sorbitol or mannitol may be employed in the instant dentifrice compositions, such are used as an aqueous solution, they may be employed herein, with the proviso, however, that it be substantially anhydrous.

The preferred liquid vehicle is an anhydrous humectant or oil selected from the group consisting of glycerine, propylene glycol, polyethylene glycol, polypropylene glycol, liquid light petrolatum, mineral oil, vegetable oil and suitable mixtures thereof.

The gelling agents is desirably selected from the group consisting of sodium carboxymethyl cellulose, hydroxyethyl cellulose, polyvinyl alcohol, Irish moss, silica aerogel or mixtures thereof.

In the preparation of dentifrice powders, it is usually sufficient to admix mechanically, e.g., by milling, the various solid ingredients, in appropriate quantities and particle sizes and thereafter carrying out procedures known in the art for packaging such powdered or tablet dentifrice compositions.

In chewable dental tablets the solids and liquids are proportioned similarly to the amounts in dental creams and the flavor is blended with the solids and liquids, and a waxy matrix such as polyethylene glycol having a molecular weight of about 6,000 by weight, generally in amounts between about 4 and about 20 percent by weight, in order to facilitate the formation of a tablet of the desired size and shape.

The listing of polishing agents, and other listings of other components of the dentifrice composition given in the present specifications are not intended to be exhaustive and therefore, for other materials of these types reference should be made to a standard handbook, such as Cosmetics: Science and Technology, by Saccharin, 2nd printing, 1963, published by Interscience Publishers, Inc.

Organic surface-active agents are generally employed in dentifrice compositions to assist in achieving thorough and complete dispersion of the components of instant compositions throughout the oral cavity during use and render the instant compositions more cosmetically acceptable. The organic surface-active material may be anionic, nonionic, ampholytic, or cationic in nature, and it is preferred to employ a surface-active agent which imparts to the composition detersive and foaming properties. Suitably such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1.2-dihydroxy propane sulfonates, and the substantially saturated high aliphatic acyl amides of lower aliphatic amino carboxylic acid compounds, such as those having 12 to 16 carbon atoms in the fatty acid, or acyl radicals, and the like. Examples of the last mentioned amides are N-lauroyl sarcosine, and the sodium potassium and ethanolamine salts of N-lauroyl, N-myristoyl, or N-palmitoyl sarcosine which should be substantially free from soap or similar higher fatty acid material which tends to substantiall reduce the effect of these compounds.

Other suitable surface-active materials include nonionic agents such as condensates of sorbitan monostearate with approximately 20 moles of ethylene oxide, condensates of ethylene oxide with propylene oxide, condensates of propylene glycol ("Pluronics"), and amphoteric agents such a quaternized imidazole derivatives which are available under the trademark "Miranol" such as Miranol $C_2M$.

Other suitable nonionic detergents are the condensation products of an alpha olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to about 1600 and containing 40% to 80% by weight of ethylene oxide, with an $\alpha$-olefin oxide to polyhydric alcohol mole ratio in the range of about 1:1 to 1:3. These detergents are manufactured using well-known polymerization techniques under conditions of high temperature and high pressure. These nonionic detergents may be mixed with similar nonionic detergents as well as other types nonionic detergents described herein.

There may also be employed olefin sulfonate detergents, typically long chain alkenyl sulfonates.

It is typical to use an effective amount of at least one surface-active material and generally between about 0.05 and 10% by weight and preferably between about 0.5 and 5% of at least one of the foregoing surface-active materials in the instant oral preparations.

Various other compatible and suitable materials may be incorporated in the effervescent dentifrice compositions of this invention. Examples thereof are coloring or whitening agents or dyestuffs, preservatives, silicones, chlorophyll compounds, ammoniated materials such as urea, diammonium phosphate and mixtures thereof, and other constituents. Further, other gas-generating agents may be employed in some instances. For example, an acid/base reaction couple may be employed when an additional in situ source of a gas is desired, e.g., see U.S. Pat. No. 3,629,468. These additional ingredients may be incorporated in the instant compositions in amounts which do not substantially adversely affect the properties and characteristics desired and are selected and used in proper amount depending upon the particular type of dentifrice composition desired.

Antibacterial agents may also be employed in the preparation of the instant dentifrice compositions to provide a total content of such agents of up to about 10% by weight, preferably about 0.01 to 5.0% by weight, most preferably about 0.5 to 1.0% by weight, based on the total weight of the dentifrice.

The dentifrice compositions may be prepared by suitably mixing the ingredients. For instance in making a cream dentifrice, e.g., a toothpaste, a gelling agent such as silica aerogel or Carbopol 934 and a preservative such as dried benzoic acid, if employed, fluoride and sweetener, if used, is dispersed with a humectant such as glycerine. Dental abrasive agents, including the gas-containing inorganic oxide material, surface-active agent and flavor are then separately added and uniformly dispersed. The toothpaste is then thoroughly degassed (e.g., in vacuo) and tubed.

EXAMPLE 1

A carbon dioxide-containing zeolite was prepared using the sodium form of zeolite A. A sample of the zeolite A was placed in a cold air purged oven. The oven was heated to 480° C. and maintained at this temperature for 1.5 hours to remove water from the zeolite. The oven and dehydrated zeolite sample were then cooled to 300° C. The dehydrated zeolite A was then placed in a container which had been purged with carbon dioxide for fifteen minutes prior to introduction of the dehydrated zeolite sample. The dehydrated zeolite sample remained in the container for 2 hours while carbon dioxide was introduced at a pressure of 8 psig and the container was vented to atmospheric pressure. After two hours the container was sealed and the carbon dioxide-containing zeolite A maintained under a carbon dioxide atmosphere. A portion of the carbon dioxide-containing zeolite A was analyzed and contained 13.37 percent by weight carbon dioxide based on the weight of the zeolite.

EXAMPL 2

Example 1 was repeated except that a Y zeolite was employed instead of zeolite A. A portion of the carbon dioxide-containing zeolite Y was analyzed and contained 15.35 percent by weight carbon dioxide based on the weight of the zeolite.

EXAMPLE 3

A dentifrice composition was prepared using the carbon dioxide-containing Y zeolite prepared in example 2. The essentially anhydrous dentifrice was prepared by placing all of the components for preparation of the dentifrice in a glove box having a nitrogen atmosphere and the preparation of the dentifrice was carried out under a nitrogen atmosphere. A slurry was formed by mixing 21.9 grams of the anhydrous carbon dioxide-containing Y zeolite with 26.75 grams of propylene glycol. This slurry was mixed with 0.075 grams benzoic acid, 0.3 grams of a silica sold under the trademark SYLOID 44, 1.00 gram sodium lauryl sulfate, 0 35 grams peppermint oil and 0.75 grams hydroxypropyl cellulose. The mixture was blended and placed in a desiccator with an aspirator attached thereto. A portion of the final dentifrice composition was added to water and observed without stirring to form a foam as carbon dioxide was released from the carbon dioxide-containing Y zeolite.

EXAMPLE 4

Example 3 was repeated except that the carbon dioxide-containing zeolite A of example 1 was employed to form the dentifrice composition. The composition was observed to form a foam upon addition to water as carbon dioxide was released from the carbon dioxide-containing zeolite A.

EXAMPLE 5

Example 4 was repeated except that the peppermint oil was replaced by an artificial sweetener. The dentifrice composition was observed to form a foam on contact with water as carbon dioxide was released from the carbon dioxide-containing zeolite.

EXAMPLE 6

The effect temperature on the effervescent activity of the dentifrice composition of example 4 was evaluated by evaluating the effervescent time for three samples (2 grams each). Each sample was placed in 500 milliliters of water having temperatures of 18° C., 32° C. and 50° C., respectively. The three samples were observed and the time recorded at which effervescent began and ended for each sample. The results were as follows:

| Water Temperature | Initial Effervescence | Ending Effervescence |
|---|---|---|
| 18° C. | 35 sec. | 7 min., 53 sec. |
| 32° C. | 15 sec. | 7 min., 30 sec. |

| Water Temperature | Initial Effervescence | Ending Effervescence |
|---|---|---|
| 50° C. | 5 sec. | 3 min., 37 sec. |

The results indicate that more rapid effervescence occurs at higher temperatures, i.e., that adsorbed gas is desorbed more rapidly at higher temperatures.

EXAMPLE 7

A dentifrice composition was formed according to the procedure of example 4 using 21.98 grams of the carbon-dioxide-containing zeolite A of example 2, 53.5 grams propylene glycol, 0.15 grams of benzoic acid, 2.0 grams of sodium lauryl sulfate, 0.2 grams of SYLOID/244, 0.25 grams of an artificial sweetener and 1.50 grams hydroxypropyl cellulose. The final dentifrice composition had a paste consistency and was placed in a dry aluminum tube and sealed to evaluate the stability of the composition with time. The dimensions of the tube were measured after filling and three (3) days after filling to determine if tube dimensions changed with time, which would indicate carbon dioxide loss by the zeolite. The tube dimensions were not observed to change over the three (3) day period.

EXAMPLE 8

A dentifrice composition was formed according to the procedure of example 3 using 42.58 grams of a carbon dioxide-containing zeolite X prepared according to the procedure employed for Example 1. A portion of the carbon dioxide-containing zeolite X was analyzed and contained 7.35 percent by weight carbon dioxide based on the weight of the zeolite. The dentifrice composition was formed by using 42.58 grams of the carbon dioxide-containing X zeolite, 53.53 grams propylene glycol, 0.150 grams benzoic acid, 0.6 grams SYLOID 244, 0.14 grams saccharin, 2.0 grams sodium lauryl sulfate and 2.0 grams hydroxypropyl cellulose.

A portion of the sample was added to water and observed to provide an effervescent action.

EXAMPLE 9

A dentifrice composition was prepared using a carbon dioxide-containing zeolite A (sodium form) and was prepared according to the procedure employed in example 1. The dentifrice was prepared according to the procedure of example 4 using 30.53 grams of the carbon dioxide-containing zeolite A, 53.52 grams glycerol, 0.15 grams benzoic acid, 20 grams sodium lacryl sulfate and 8.6 grams polyethylene glycol PEG 600. A portion of the dentifrice was added to water and observed to provide foam, i.e., effervescent action, without stirring.

EXAMPLE 10

A dentifrice composition was prepared using the carbon dioxide-containing zeolite X of example 8. The dentifrice was prepared according to the procedure of example 4 using 41.04 grams of the carbon dioxide-containing zeolite X, 57.73 grams glycerol, 1.0 gram of sodium lauryl sulfate, 0.1 gram hydroxypropyl cellulose and 0.15 grams benzoic acid. A portion of the dentifrice was added to water and observed to provide an effervescent action.

What is claimed is:

1. An effervescent dentifrice composition which upon contact with water provides an effervescent action which comprises an anhydrous dentifrice base medium and from about 1 to about 60 weight percent of a dehydrated crystalline microporous inorganic oxide adsorbent containing an effective amount of between about 5 and about 25 percent by weight of carbon dioxide based on the combined weight of the said dehydrated inorganic oxide adsorbent and carbon dioxide.

2. Effervescent dentifrice composition according to claim 1 wherein the crystalline microporous inorganic oxide adsorbent is selected from the group consisting of zeolitic aluminosilicates, aluminophosphates and silicoaluminophosphates.

3. Effervescent dentifrice composition according to claim 2 wherein the crystalline microporous inorganic oxide adsorbent is a zeolitic lauminosilicate selected from the group consisting of zeolite A, zeolite B, zeolite X, zeolite Y, zeolite P, zeolite W, zeolite L, zeolite F, silicalite, analcite, chabazite, paulingite, ptilolite, ferrierite, mordenite, levynite, clinoptilolite and errionite.

4. Composition according to claim 3 wherein the zeolitic aluminosilicates contain metal cations selected from the group consisting of alkali metal, alkaline earth metal, zinc and copper.

5. The effervescent dentifrice composition according to claim 2 wherein said composition contains a liquid vehicle, said liquid vehicle being an anhydrous humectant or oil selected from the group consisting of glycerine, propylene glycol, polyethylene glycol, mannitol, polypropylene glycol, sorbitol, liquid light petrolatum, mineral oil, vegetable oil, and mixtures thereof.

6. The effervescent dentifrice composition according to claim 2 wherein said anhydrous dentifrice base medium comprises:
   (a) between about 10 and about 90 percent by weight of at least one liquid vehicle;
   (b) between about 0.05 and about 10 percent by weight of at least one surface-active agent;
   (c) between about 0.1 to about 10 percent by weight of at least one gelling agent;
   (d) between about 0.1 to about 10 percent by weight of at least one flavoring agent; and
   (e) between 0.01 and about 1.0 percent by weight of a fluorine-containing compound.

7. The effervescent dentifrice composition according to claim 1 wherein the mean particle size of said carbon dioxide-containing inorganic oxide adsorbent is less than 10 microns and has a particle size distribution wherein less than 10 per cent of the particles have a particle diameter greater than 5 microns.

8. The effervescent dentifrice composition according to claim 7 wherein less than 5 percent of said particles of carbon dioxide-containing inorganic oxide adsorbent have a mean particle size greater than 5 microns.

9. The effervescent dentifrice of claim 7 wherein said gas-containing inorganic oxide material has an RDA value less than 250.

10. The effervescent dentifrice of claim 7 wherein said RDA is between about 30 and about 120.

* * * * *